United States Patent [19]

Sato

[11] 4,165,179

[45] Aug. 21, 1979

[54] DEVICE FOR WIPING OPTICAL WINDOW IN TURBIDIMETER OR SIMILAR OPTICAL INSTRUMENT FOR EXAMINING LIQUID SAMPLE

[75] Inventor: Ko Sato, Tokyo, Japan

[73] Assignees: Nippon Precision Optical Instrument Co., Ltd.; Nippon S R S, Inc., both of Tokyo, Japan

[21] Appl. No.: 815,088

[22] Filed: Jul. 13, 1977

[30] Foreign Application Priority Data

Aug. 19, 1976 [JP] Japan .................................. 51-98159
Mar. 10, 1977 [JP] Japan .................................. 52-25390

[51] Int. Cl.² .......................................... G01N 21/24
[52] U.S. Cl. ...................................... 356/246; 350/61
[58] Field of Search ............... 350/61; 356/208, 246; 250/573, 574, 576; 134/166 R; 15/21 E, 22 A, 56, 59, 65, 68; 73/324

[56] References Cited

U.S. PATENT DOCUMENTS

| | | | |
|---|---|---|---|
| 1,234,191 | 7/1917 | Mahaley | 73/324 |
| 1,252,656 | 1/1918 | Breen | 73/324 |
| 2,866,379 | 12/1958 | Veit | 15/68 X |
| 2,911,665 | 11/1959 | Mackiewicz et al. | 15/56 X |

*Primary Examiner*—John K. Corbin
*Assistant Examiner*—Matthew W. Koren
*Attorney, Agent, or Firm*—Kurt Kelman

[57] ABSTRACT

Disclosed herein is a device for wiping the optical window of a sample cell in a turbidimeter or other optical instrument for examining a liquid sample, which device comprises a wiper adapted to be inserted into the inner surface of the sample cell and rotated around its axis so as to clean the optical window quickly and easily of defiling matter adhering to the optical window.

2 Claims, 6 Drawing Figures

DEVICE FOR WIPING OPTICAL WINDOW IN TURBIDIMETER OR SIMILAR OPTICAL INSTRUMENT FOR EXAMINING LIQUID SAMPLE

BACKGROUND OF THE INVENTION

This invention relates to a device for wiping the optical window in a turbidimeter or other similar optical instrument for examining a liquid sample. More particularly, the present invention relates to a method and device for easily and quickly wiping the inner surface of a sample cell in a turbidimeter or other similar optical instrument which has the sample cell provided therein as part of the path for a liquid sample at a position falling within the path of light extending from a light source to a measuring unit, so that the degree by which the beam of light emitted from said light source in the direction of the measuring unit is attenuated by suspended solid particles present in the liquid sample in motion through the sample cell is measured on the measuring unit and, based on the result of the measurement, the content of the suspended solid particles in the liquid sample is determined.

It is widely known that a turbidimeter designed to determine the amount of suspended solid particles contained in a given liquid sample in terms of turbidity, for example, makes use of an integrating sphere (an Ulbricht sphere) as means for measuring the amount of incident light and effects determination of the turbidity of the liquid sample by a procedure comprising the steps of projecting a collimated beam of light from a light source toward the integrating sphere, allowing the beam of light to pass into a sample cell so that during the passage of the beam of light through the sample cell, the part of the beam of light which impinges upon the suspended solid particles present in the liquid sample held inside the sample cell is diffused and the remaining part of the beam of light which escapes the impingement is allowed to advance straight through the sample cell, measuring the intensity of the diffused light and that of the undiffused light on separate light-receiving elements annexed to the integrating sphere and comparing the measured intensities. Needless to say, the means for measurement of the amount of incident light is not limited to the integrating sphere. For any measuring instrument of the type which is designed to accomplish the determination of the amount of suspended solid particles present in a liquid sample by causing a beam of light issuing from a light source to pass through a sample cell for thereby having the beam of light attenuated by suspended solid particles contained in the liquid sample and measuring the degree of the attenuation, however, when the inner surface of the sample cell which falls in the path for the beam of light happens to be smeared with a remnant of the suspended solid particles contained in the liquid sample passed through the sample cell in the previous test run, then the value of measurement obtained by the instrument is inclusive of a portion ascribable to the solid particles adhering to the cell surface in the path for the beam of light and, therefore, fails to represent exactly the amount of suspended solid particles contained in the liquid sample under test. The smear of the cell surface thus prevents the instrument from providing an accurate measurement, no matter whether the precision of the turbidity itself may be improved even to a point where the turbidity will be accurately measured to the finest degree.

For this reason, there have been proposed measures for cleaning the inner surface of the sample cell to remove adhering solid particles by means of ultrasonic waves or water jets. The proposed measures in their existing state, however, are not effective enough to provide thorough removal of the adhering solid particles. In the circumstances, there is still adopted a method whereby the instrument is disassembled to remove the sample cell therefrom and the inner surface of the sample cell is wiped manually. According to this manual method, the instrument must be disassembled to permit removal of the sample cell and reassembled after completion of the wiping work. Thus, the wiping work inevitably keeps the instrument out of service for a long time and entails much time and labor in the disassembling and reassembling works.

SUMMARY OF THE INVENTION

An object of the present invention is to provide a device for wiping the optical window, namely the inner surface of the sample cell in an optical instrument for the determination of the amount of suspended solid particles in a liquid sample, which device provides quick and perfect wiping of the optical window without requiring the instrument to be disassembled to permit removal of defiling matter on the inner surface of the sample cell.

To accomplish the object described above in accordance with the present invention, there is provided a device of the following construction for wiping the optical window: In case where the sample cell having an optical window is cylindrical in shape and is disposed in a lateral direction, the device of this invention comprises a three-way pipe of the shape of the letter T disposed in such a position as to have one end thereof connected to at least one end of the sample cell and a wiper inserted into the main tube through the remaining end thereof, whereby the inner surface of the optical window is given necessary wiping by causing the wiper to produce reciprocating and rotating motions. In case where the sample cell having the optical window is cylindrical in shape and is disposed in a longitudinal direction, then the device of this invention comprises a wiper disposed at a position selected so as not to interfere with the path for the beam of light across the sample cell and the path for the liquid sample through the sample cell, whereby the inner surface of the optical window is given required wiping by causing the wiper to be moved to the optical window and then turned around its axis either periodically or whenever the inner surface of the sample cell is smeared.

The device for wiping the optical window provided by the present invention can be operated to give thorough wiping to the inner surface of the sample cell without requiring the measuring instrument to be disassembled. Thus, it permits the wiping operation to be carried out quickly and perfectly.

Other objects and characteristic features of the present invention will become apparent from the description to be given in detail hereinbelow with reference to the accompanying drawings.

DESCRIPTION OF THE PREFERRED EMBODIMENTS

Figure 1:
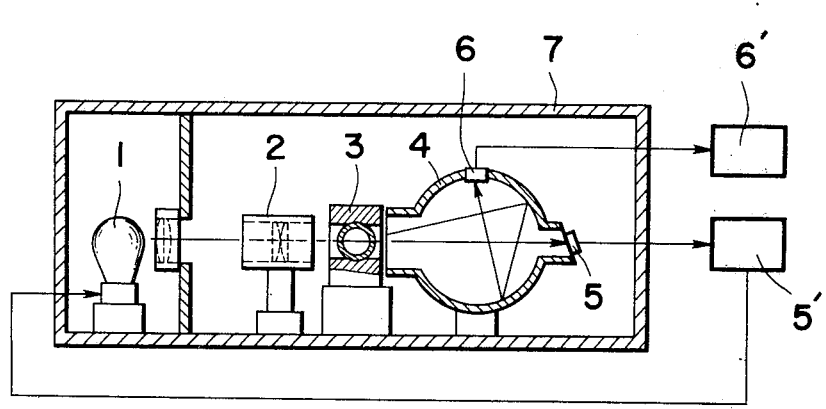
FIG. 1 is a sectional side view illustrating schematically a turbidimeter.

With reference to FIG. 1, the light issuing from a light source 1 such as a tungsten lamp or laser is converted by a collimator lens system 2 into a collimated beam of light, passed through a transparent sample cell 3 forming a part of a sample conduit for passing a liquid sample and into an integrating sphere illustrated herein as a light-receiving unit 4, with the portion of the light still constituting a collimated beam (the undiffused beam) received in one element 5 and the diffused portion of the light received in the other element 6. The beams thus received in the two elements are amplified by the amplifiers 5', 6' respectively and the amplified intensities are compared. By continuing this procedure, the turbidity of the liquid sample being sent through the sample cell 3 can be continuously measured with a measuring circuit (not shown). In this case, by negatively feeding back of a part of the electrical output of the non-diffused light obtained at the amplifier 5' to the light source 1, the turbidity of the liquid sample can be determined without use of a circuit which would otherwise be required for computing the ratio of the diffused light to the undiffused light and, at the same time, the anxiety about possible instability of output due to the phenomenon of drift of the light source can be eliminated.

Generally, the light source 1, the optical system 2, the part of sample conduit including the sample cell 3 and the light-receiving unit 4 are disposed within a housing 7.

Figure 2:
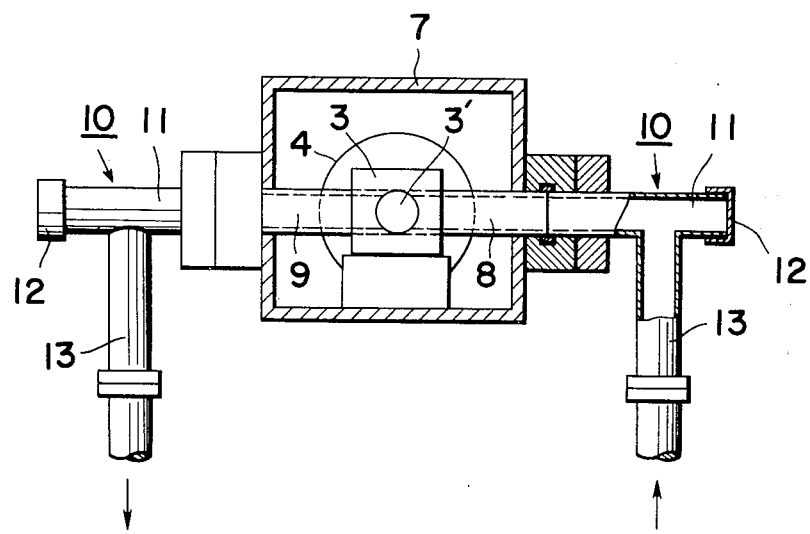
FIG. 2 is a front view of the device of the present invention for wiping the optical window as put to use in the turbidimeter of FIG. 1, partially cut away to show the state of measurement.
Figure 3:
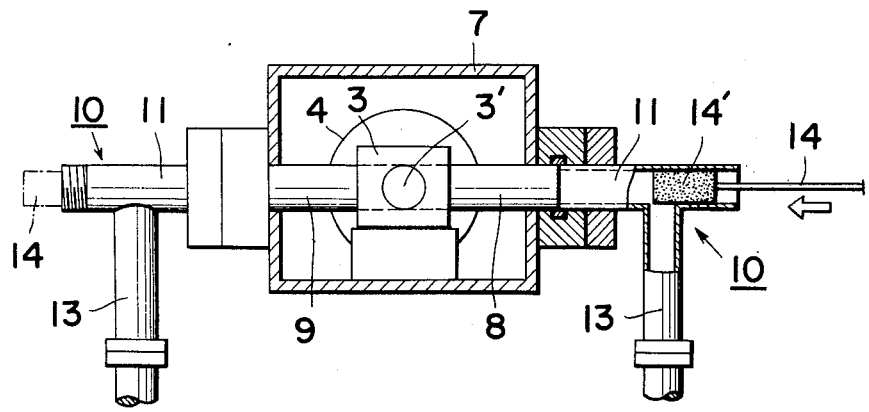
FIG. 3 is a front view of the device of FIG. 2 in the process of starting a wiping motion.

To the lateral sides of the sample cell 3 are connected pipes 8, 9 which extend past the side walls of the housing 7 and serve to supply a sample to the sample cell 3 and discharge the used sample from the sample cell 3 respectively (as shown in FIG. 2). Three-way T-shaped pipe 10 each possessed of a main tube 11 are connected one each to the outer ends of the pipes 8, 9 extending from the housing 7, with the inner ends of the main tubes 11 joined in a leakproof manner to the outer ends of the pipes 8, 9 and the outer ends of the main tubes 11 stoppered detachably each with a cap or plug 12. For the determination of turbidity, therefore, a given liquid sample is introduced through a branch tube 13 of one of the two three-way pipes, then forwarded through the pipe 8, the cell 3 and the pipe 9 and finally discharged through a branch tube 13 of the other three-way pipe while the caps or plugs 12 are kept in position at the outer ends of the main tubes. When the inner surface of an optical window 3' of the sample cell 3 through which the beam of light passes becomes smeared because of adhesion of solid particles suspended in the liquid sample, for example, the supply of the liquid sample is discontinued and the cap or plug 12 on either or both of the two three-way pipes is removed to open the outer end of the main tube of at least one three-way pipe. A wiper 14 having a brush 14' attached to the leading end of a long handle is inserted into the main tube through the opened outer end, so that the smear adhering to the inner surface of the optical window 3' is rubbed off with the brush 14' (FIG. 3).

The brush 14' of the wiper 14 is not necessarily limited to the type having a tuft of hairs or bristles attached radially to a handle but may be of the type having a wad of soft cloth or polyurethane foam wrapped around a handle. Literally, anything can be used insofar as it fulfils the purpose of rubbing the inner surface of the optical window and removing the smear adhering to the surface.

The ease with which the wiper is operated can be improved generally by giving the pipes 8, 9 the same inner shape as that of the sample cell 3 and giving the brush 14' a slightly larger outer shape than the inner shape of the pipes so that required removal of the adhering smear will be obtained by simply pushing in the wiper or by simultaneously pushing in and rotating the wiper.

When the wiping of the optical window is finished, the wiper is pulled out of the sample cell and the wiping device and the cap or plug is replaced on the outer end of the main tube, making the instrument ready for continued service.

According to this particular embodiment of the present invention, whenever the smear on the optical window of the sample cell has reached an intolerable degree, the operation of the instrument can be discontinued and the wiping device readily put to use as described above to remove the smear adhering to the inner surface of the optical window of the sample cell. In such case, the wiping can be carried out without requiring the troublesome work of disassembling the instrument to remove the sample cell from the housing and reassembling the instrument after completion of the wiping. The interruption of the operation of the instrument by the wiping work is very short so that the operation of the instrument can be performed practically continuously.

It may suffice to have only one three-way pipe attached to either of the two pipes 8, 9. From the two three-way pipes attached one each to the two pipes 8, 9 there is derived an advantage that whenever wiping work is to be carried out, an unobstructed passage for the wiper can be formed by removing the caps or plugs from the outer ends of the main tubes of the three-way pipes so that the brush of the wiper inserted into the unobstructed passage through one of the two three-way pipes may be thrust out of the other three-way pipe to permit removal of the dirt collected on the brush and, after the brush has been cleaned, the brush may be worked in the opposite direction to give the inner surface of the optical window a final wiping.

Figure 4:
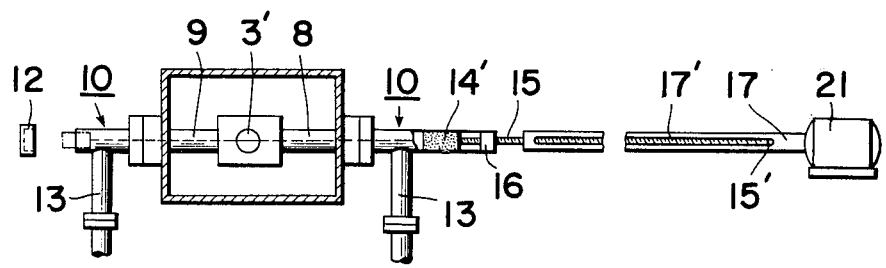
FIG. 4 is a front view of another embodiment of the wiping device of the present invention.
Figure 5:
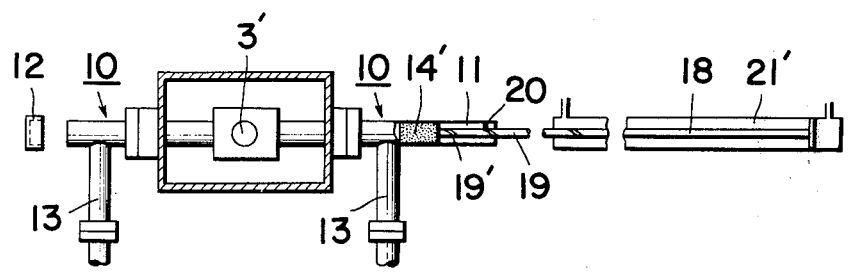
FIG. 5 is a front view of still another embodiment of the wiping device of the present invention.

FIGS. 4 and 5 illustrate other embodiments of the invention whereby the wiping work is carried out each by use of a powered wiper.

A portion of the wiper 14 containing the brush 14' is set in position inside the main tube 11 of one of the three-way pipes 10 connected to one pipe 8. While the instrument is in use, the brush 14' is kept ready for service outside the point where the branch tube 13 meets the main tube 11 so that the brush will not interfere with the operation of the instrument. The brush 14' held in this position concurrently filfils the role which is discharged in the previous embodiment by the plug 12 in preventing the liquid sample from flowing out of the free end of the main tube while the instrument is in use.

In the embodiment of FIG. 4, the handle of the wiper 14 is threaded with a male screw and a member 16 having this threaded handle screwed into a female screw formed therein is set in position inside the free end of the main tube. The portion of the handle 15 protruding from the free end of the main tube is inserted into a long cylindrical shaft 17, for example, which is rotated by a reversible motor 21. The slot 17' axially formed in the cylindrical shaft 17 is coupled with the projection 15' formed on the handle 15 so as to establish the relationship of a slide key so that the motion of the cylindrical shaft 17 only imparts a rotational movement to the handle, with the result that the handle 15 will be helically advanced or retracted by the member 16.

When the wiping work is to be carried out, the supply of the liquid sample is discontinued and the motor is set to operation. Consequently, the wiper is helically advanced integrally with its handle 15 so that the brush 14' will wipe the smear adhering to the inner surface of the optical window 3'. After the work, the brush can be returned to its original waiting position by operating the motor in the reversed direction and helically retracting the handle. Limit switches so positioned as to detect the arrival of the brush 14' at the farthest reach of its travel and the return of the brush to its original waiting position enable the motor operation to be automatically stopped.

The embodiment illustrated in FIG. 4 is designed to operate the wiper by means of a rotary actuator or motor 21, whereas the embodiment of FIG. 5 is so adapted as to operate the wiper by means of a linear-motion actuator 21' which is represented by a hydraulically operated piston cylinder. The piston cylinder is desired to be of a double acting type which produces a reciprocating motion. To the rod end of this piston rod 18 is connected the rear end of the handle 19 of the wiper. By the operation of this piston cylinder, the brush of the wiper can be driven forward from its waiting position to wipe the inner surface of the optical window and remove the smear adhering to the surface. After the wiping work, the brush is driven back to its original waiting position. In this embodiment, the wiper can be made to automatically produce a rotation around its axis while it is in an axial motion by for example, providing the handle 19 thereof with a helical groove 19' on the periphery thereof and causing the projection 20 provided on the other end of the main tube 11 to be meshed with the helical groove 19'. Desirably in this case, the handle 19 and the piston rod 18 are rotatably joined relative to each other.

In the embodiments illustrated in FIGS. 4 and 5, the remaining pipes 9 each have a three-way pipe connected thereto. The main tubes of these pipes 10 have their free ends stoppered with a cap or plug 12. The cap or plug is removed from the main tube when the wiping work is to be started. The removal of the cap or plug is necessary because, during the wiping work, the brush can be pushed past the sample cell to the extent of thrusting out of the opened free end of the main tube in the three-way pipe and the dirt which has been removed from the optical window and lodged in the brush can be removed while the brush is held in the thrust position before the brush is retracted past the sample cell. Where this necessity is not felt, no three-way pipe need be connected to the pipe 9.

The embodiments so far described have invariably been concerned with devices designed to give a wiping to optical windows in sample cells which are cylindrical in shape and are disposed in a lateral direction. Now, an embodiment of the device adapted to provide a wiping of cylindrical sample cells disposed in a longitudinal direction will be described with reference to FIG. 6.

Figure 6:
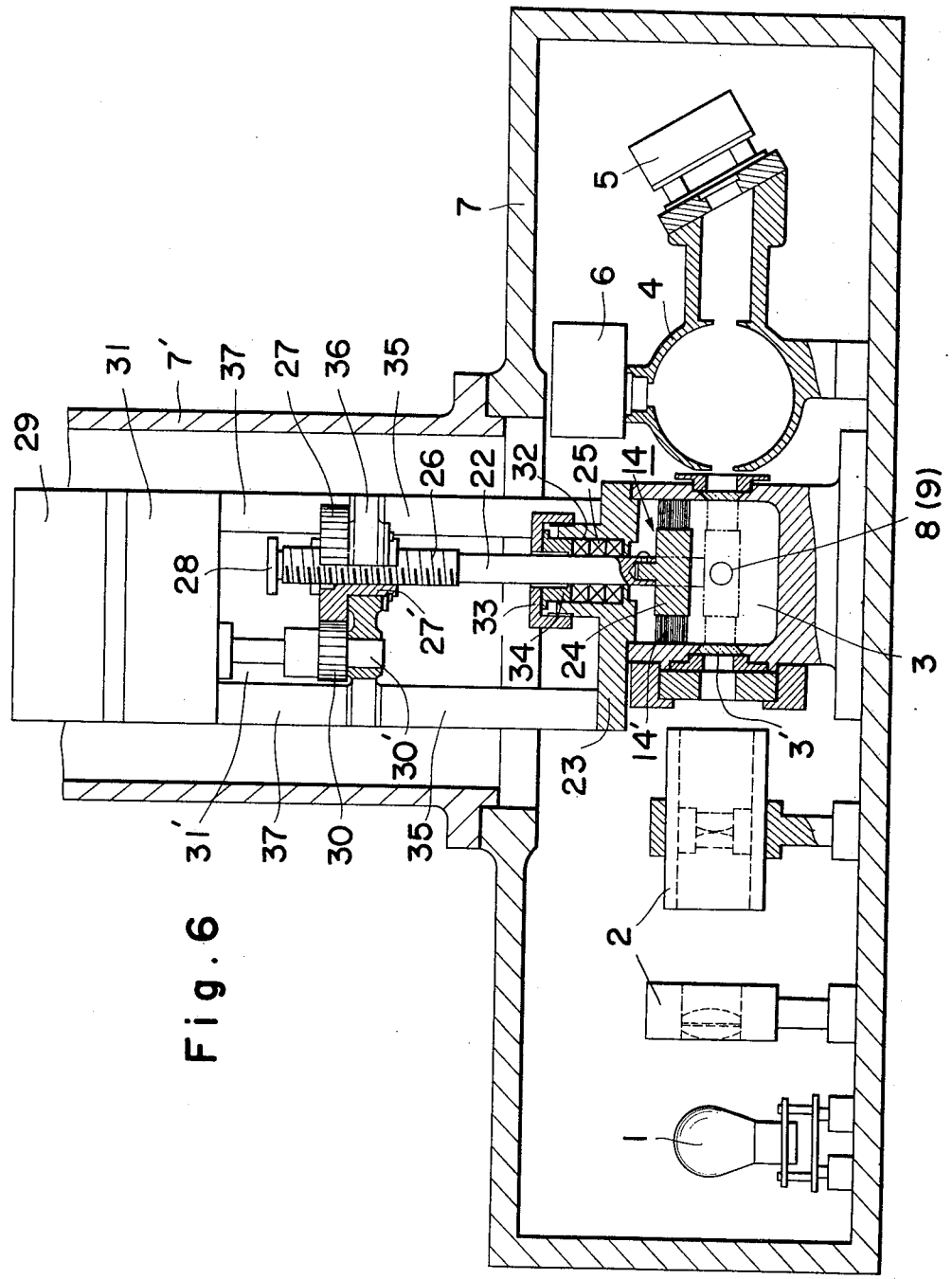
FIG. 6 is a front view of yet another embodiment of the wiping device of the present invention.

In FIG. 6, the light issuing from a light source 1 is converted such as by a collimator lens system 2, for example, into a collimated beam of light, passed into a transparent sample cell 3 constituting part of a sample path for transporting a liquid sample and then into an integrating sphere represented as a light-receiving unit 4, with the collimated beam of light (undiffused light) received on one light-receiving element 5 provided inside the sphere and the light trap and the diffused beam of light received on the other light-receiving element 6. By comparison of the intensities of the beams of light received by two elements 5, 6, the trubidity of the liquid sample being sent through the sample cell 3 can be determined. The procedure is known to the art and is similar to that of the embodiments described previously.

In this embodiment, the transparent cylindrical sample cell 3 is disposed in a longitudinal direction on the optical axis connecting the light source 1 and the light-receiving unit 4. The liquid sample is fed into and discharged from the sample cell in directions perpendicular to the optical axis through an inlet pipe 8 and an outlet pipe 9. Inside the sample cell 3, the wiper 14 attached to a shaft 22 penetrating through the lid 23 of the sample cell 3 is set in position above the optical axis. In this embodiment, the wiper 14 is composed of a base plate 24 fastened replaceably to the lower end of the shaft 22 and a brush 14' having its component bristles planted radially on the periphery of the base plate 24. The bristles of the brush 14' are long so that their tips are held in sliding contact with the inner surface of the optical window 3' of the sample cell 3. Alternatively the wiper 14 may be made of a soft cloth or spongy article bulky enough to remain in sliding contact with the inner surface of the optical window of the sample cell, for example.

The shaft 22 is held fast in position by being squeezed circumferentially by a packing 25 which is incorporated in the lid 23 of the cell. The portion of the shaft 22 which protrudes upwardly from the lid 23 is provided at the upper part with a male screw 26 and is driven past a gear 27 rotatably supported above the sample cell, with the male screw 26 meshed with an internal screw formed at the center of the gear 27. To the upper tip of the shaft 22 is attached a clutch plate 28. And, the gear 27 is interlocked to and rotated by a driving gear 30 which is interlocked to a motor 29 and a speed reducer 31 so as to be rotated at a reduced speed.

The packing 25 is set in position inside a hole 32 provided in the lid 23 of the sample cell, pressed tightly against the bottom of the hole 32 with a setscrew 33 and a presser member 34, and adapted to hold the shaft 22 fast in position by squeezing the shaft circumferentially. Further in the present embodiment, several pillars 35 are erected on the lid 23 of the cell 3 and a supporting plate 36 is horizontally mounted on these pillars. On the supporting plate 36, second pillars 37 are erected opposite the first pillars 35 to support thereon a motor 29 and a speed reducer 31. Screws tighten into rigid union the motor 29, the reducer 31, the pillars 37, supporting plate 36, pillars 35 and the lid 23. The downward shaft member 30' of the driving gear 30 fastened in screwed engagement to the lower end of the speed reducer shaft 31' having the driving gear 30 attached thereto is pivotally supported on the supporting plate 36 and, at the same time, the downward tubular member 27' having an extension of the internally cut screw of the gear 27 formed on the inner wall thereof is pierced downwardly through the supporting plate 36 and fastened at the lower end thereof such as to a snap ring, so that the tubular member 27' may be prevented from coming loose upwardly through the supporting plate 36 and the gear 27 may be rotated on the supporting plate 36.

In order to cause the wiper 14 kept in waiting position above the optical path of the sample cell 3 to provide a wiping of the inner surface of the optical window 3' of the sample cell, the motor 29 is set to operation to rotate the gear 27 in one direction through the medium of the driving gear 30. This rotation of the gear 27, though incapable of rotating the shaft 22 which is held fast in position by being squeezed circumferentially, causes the shaft 22 to go downwardly because the male screw 26 is meshed with the internal screw formed at the center of the gear 27. Consequently, the wiper 14 which is provided at the leading end of the shaft 22 is brought down to the position corresponding to the optical window 3' in the sample cell 3 as indicated by a dotted line. At the time that the wiper 14 has reached the position corresponding to the optical window 3', the clutch plate 28 provided at the upper end of the shaft 22 comes into pressing contact downwardly with the gear 27 and consequently the shaft 22 begins to rotate in conjunction with the gear 27 while overcoming the squeezing force of the packing 25, bringing the downward motion of the shaft 22 to a stop. The rotation thus produced causes the wiper 14 to rotate inside the optical window of the sample cell to wipe the inner surface of the optical window thoroughly. If there is incorporated a system wherein a limit switch or some other similar means functions to detect the fact that the clutch plate 28 has come into pressed contact with the gear 27 or the shaft 22 has fallen a prescribed distance and, upon this detection, a timer is actuated, then the reverse rotation of the motor 29 can be started after lapse of a fixed time (several minutes being sufficient) to complete the wiping work. The gear 27 can also be started to a reverse rotation by manually or automatically giving a signal to the motor after the wiping work has been continued for a length of time considered necessary. As the gear is rotated in this direction, the clutch plate 28 is deprived of its force in the direction of the gear 27, with the result that the shaft 22 is held fast by the packing 25 and is consequently caused to discontinue its rotation but is allowed to continue its ascending motion. Thus, the wiper 14 is returned to its waiting position above the optical path in the cell. The reverse rotation of the motor is stopped by a timer on which the timer required for the wiper 14 to return to its original waiting position has been set in advance or by a limit switch which functions to detect the fact that the shaft 22 has reached its upper limit of its ascending motion. After the motor has stopped, the measurement with the instrument can be resumed.

The force with which the packing 25 holds the shaft 22 is adjusted by properly regulating the tightness with which the setscrew 33 is fastened, so that the packing allows the shaft to start rotating at the time that the clutch plate 28 comes into pressed contact downwardly with the gear 27.

The present embodiment wherein the shaft is held by the packing 25 requires use of only one motor to move the wiper 14 from its waiting position to the position opposite the optical window and, conversely, return the wiper 14 from the position opposite the optical window to the original waiting position and, by having the clutch plate 28 brought into pressed contact downwardly with the gear 27, cause the wiper to rotate inside the optical window. The packing 25 and the clutch 28, while held in the state of pressed contact, cooperate and constitute a conversion device for changing the manner in which the force of the motor is utilized. This combination of a packing 25 and a clutch plate 28 cooperatively functioning as the conversion device is merely one example of such a conversion device. The same function can be attained by adopting some other construction so far as there is produced the same operation.

Further, in this embodiment, the liquid sample under test does not leak through the gap between the lid 23 and the shaft 22 because the packing 25 effectively squeezes the shaft 22 circumferentially.

The light source 1, the cell 3 and the light-receiving unit 4 are disposed inside the housing 7. The portion of the housing which falls directly above the cell is left open to permit attachment of a cover 7' which serves to protect the pillars 35, 37, the supporting plate 36 and the motor 29. When the wiper 14 has worn out to the extent of requiring replacement, therefore, the replacement can be accomplished after the cover 7' has been taken off the housing and the lid 23 of the cell has been removed from the cell proper. When the packing 25 has worn out by use, it can be replaced after the wiper has been removed in the manner described above, the assembly of pillars 35, 37 and a supporting plate 36 has been taken off the upper wall to permit withdrawal of the shaft 22 and the setscrew 33 has been removed.

Although the waiting position of the wiper is illustrated as falling above the optical window of the cell in the present embodiment, it may of course be fixed below the optical window. As convenience dictates, the waiting position may be on the lateral side insofar as the wiper held in that position does not interfere with the path for the liquid sample or to the path of light.

As is clear from the foregoing description, the device of the present invention for wiping the optical window in the optical measuring instrument provides safe and quick wiping of the optical window and enables the wiper to be readily operated with motive force. When this device is used with an automatic measuring instrument, therefore, the optical window of the instrument can be wiped at any desired time or at fixed intervals by remote control, so that the values of measurement made by the instrument are accurate and reliable because they are not affected by otherwise possible heavy smear of the optical window.

What is claimed is:

1. A device for wiping an optical window of a sample cell of an optical instrument for examining a liquid sample in the sample cell, which comprises a shaft having a leading end inserted in said sample cell, a wiper attached to the leading shaft end, a motor arranged to operate said shaft, and means effective upon operation of said motor for linearly and non-rotatively moving said shaft and wiper between a waiting position remote from said optical window and a wiping position opposite said window, and for rotating said shaft and wiper only in said wiping position.

2. The wiping device of claim 1, wherein said moving and rotating means comprises a gear arranged to be rotated by said motor, said gear having an internal thread, an external thread on said shaft and meshing with said internal gear thread, a packing arranged to squeeze said shaft circumferentially and thereby to prevent rotation of said shaft, and a clutch plate arranged on said shaft to make pressure contact with said gear in said wiping position and thereby to transmit a rotational force to said shaft sufficient to overcome the squeezing force of said packing.

* * * * *